United States Patent [19]

Frulla et al.

[11] 4,039,581

[45] Aug. 2, 1977

[54] PROCESS FOR THE PREPARATION OF DI(AMINO PHENYL)METHANES

[75] Inventors: Floro F. Frulla, Wallingford; Adnan A. R. Sayigh, North Haven; Henri Ulrich, Northford; Peter J. Whitman, Hamden, all of Conn.

[73] Assignee: The Upjohn Company, Kalamazoo, Mich.

[21] Appl. No.: 590,801

[22] Filed: June 27, 1975

[51] Int. Cl.² ............................................. C07C 85/08
[52] U.S. Cl. ........................ 260/570 D; 260/2.5 AT; 260/453 AM; 260/570.5 P; 260/570.9
[58] Field of Search ................... 260/570 D, 453 AM

[56] References Cited

U.S. PATENT DOCUMENTS

| 3,362,979 | 1/1968 | Bentley | 260/570 |
| 3,676,497 | 7/1972 | Recchia et al. | 260/570 |
| 3,857,890 | 12/1974 | Recchia et al. | 260/570 |

FOREIGN PATENT DOCUMENTS

| 963,422 | 7/1964 | United Kingdom | 260/570 |
| 1,163,810 | 9/1969 | United Kingdom | 260/570 |

*Primary Examiner*—Robert V. Hines
*Attorney, Agent, or Firm*—Denis A. Firth; John Kekich

[57] ABSTRACT

Aniline and formaldehyde are condensed (2–10 moles aniline per mole of formaldehyde) at ambient temperature in the absence of acid catalysts to give a mixture of aminals (anilinoacetals) and aniline from which the water is removed. The anhydrous aminals are contacted with a solid catalyst (clays, zeolites, diatomaceous earth) using either batch or continuous operation initially at 20° C to 55° C until benzylamine formation is substantially complete, then at 50° C to 65° C until benzylamine conversion to methylene polyphenyl polyamines is 75 – 90% complete and finally at 80° C to 100° C. A polyamine mixture is obtained in which diaminodiphenylmethane is the major (order of 90 percent by weight or higher) component, the bulk of the higher oligomeric polyamines being triamine. The diaminodiphenylmethane component contains of the order of 85 percent of 4,4'-isomer, the rest being 2,4'-isomer except for very small amounts (order of 2 percent or less) of 2,2'-isomer.

Advantages of the process include high yield of diaminodiphenylmethane with relatively high 4,4'-isomer content, low oligomeric polyamine content, low temperature operation (energy consumption lower), no acidic reactants to cause corrosion of equipment, and rapid rates of conversion.

13 Claims, No Drawings

PROCESS FOR THE PREPARATION OF DI(AMINO PHENYL)METHANES

BACKGROUND OF THE INVENTION

1. Field of the Invention

This invention relates to the preparation of polyamines and is more particularly concerned with a process for the condensation of aniline and formaldehyde to yield polyamine mixtures containing a high proportion of diaminodiphenylmethane and low oligomeric polyamine content.

2. Description of the Prior Art

The preparation of mixtures of methylene bridged polyphenyl polyamines containing diaminodiphenylmethanes by condensation of aniline and formaldehye under aqueous conditions in the presence of mineral acids, particularly hydrochloric acid, has been widely descried. Illustrative of such processes are those shown in U.S. Pat. Nos. 2,638,730; 2,950,263; 3,260,751; 3,277,173; 3,297,759; and 3,476,806. Such processes, in one form or another, are widely used commercially to prepare the polyamines in question, which polyamines are employed as intermediates in the preparation of the corresponding isocyanates, i.e. diisocyanatodiphenylmethane and mixtures of polymethylene polyphenyl polyisocyanates. The isocyanates are employed in the preparation of a variety of polyurethanes, polyisocyanurates and other polymers (both cellular and non-cellular) which can be derived from polyisocyanates.

However, the operation of processes catalyzed by aqueous mineral acid of the type described above necessarily gives rise to serious corrosion problems, involving constant repair and maintenance requirements, and increasing overhead costs in the operation of the manufacturing plants in which such processes are utilized.

Very little attention has been devoted hitherto to utilizing catalysts of a relatively non-corrosive nature. U.S. Pat. No. 3,362,979 describes the use of siliceous catalysts at elevated temperatures (125° t 300° C preferred). The aniline and aqueous formaldehyde are brought together in the presence of the catalyst at a temperature in the above range and the water introduced with the formaldehyde, as well as the water of condensation eliminated in the reaction, is removed from the reaction mixture on a continuous basis. Such a procedure does not lend itself readily to operation on a continuous basis on a commercial scale. Further, the diamine content in the product in many instances is relatively low and said diamine contains excessively high proportions of 2,4'-isomer.

British patent specification No. 1,207,377 describes a very similar process, i.e. reaction of aromatic amine and formaldehyde at elevated temperatures with continuous removal of water, but using a catalyst comprising a benzene sulfonic acid supported on an inert material. No details are given of the results of application of the process to the condensation of aniline and formaldehyde, all the specific examples being devoted to the condensation of either mono- or dichloroaniline with formaldehyde.

French Patent Specification 1,448,359 shows a similar process using, for example, a bentonite clay with removal of water from a mixture of aniline and formaldehyde while the latter is refluxed in the presence of the clay catalyst.

The above procedures have, in our hands, been found to give rise to rapid deactivation of the catalyst with consequent need to reactivate the catalyst after each run. The procedures are not readily adapted to continuous operation on the commercial scale. Further, the yield of diamine in the polyamine product is relatively low and the proportion of 2,4'-isomer present in the diamine is relatively high and certainly higher than is desirable for reasons which will be explained hereafter.

We have now found that the condensation of aniline with formaldehyde, and the conversion of the initial condensation product to the desired polyamines having high diamine content, can be effected by heterogeneous catalysis using improved procedures which are free from the problems discussed above. Not only do the procedures described below have the advantage of being corrosion free, but they also have been found to yield results which are unexpected and highly useful.

SUMMARY OF THE INVENTION

This invention comprises a process for the preparation of a mixture of di(aminophenyl)methanes and oligomeric polymethylene polyphenyl polyamines wherein the diamine content is of the order of 90 to 95 percent by weight and wherein the p,p'-isomer content of said diamine is of the order of 85 percent by weight, which process comprises the steps of a. reacting aniline and formaldehyde in a proportion within the range of 2 moles to 10 moles of aniline per mole of formaldehyde at a temperature of 10° C to 55° C and in the absence of catalyst to form a mixture of aminals;

b. separating the water from said aminals;

c. contacting said aminals, free water, with a solid catalyst selected from the class consisting of clays, zeolites and diatomaceous earth, at a temperature in the range of 20° C to 55° C until the reaction mixture contains from about 85% to 100% by weight of the corresponding benzylamines;

d. thereafter raising the temperature of the reaction mixture to about 55° C to 65° C until from about 75% to 90% of said benzylamines have been converted to methylene polyphenyl polyamines; and e. thereupon finally raising the temperature of the reaction mixture to 80° C to 100° C until conversion to methylene polyphenyl polyamines is complete.

The invention also comprises the polyamines produced by the above process and the polyisocyanates derived by phosgenation of said polyamines.

DETAILED DESCRIPTION OF THE INVENTION

In the first step of the process of the invention aniline and formaldehyde are brought together in the absence of acid or any other catalyst hitherto employed in the art. The reaction is conducted substantially in accordance with the procedure described by Cohn, Zeitschrift fuer Ang. Chem. XIV, 1901, 311. Thus the aniline and formaldehyde are brought together in any convenient manner, advantageously with stirring. The aniline can be added to the formaldehyde or vice versa. However, it is preferred to add the formaldehyde to the aniline. The formaldehyde is preferably in the form of an aqueous solution, i.e. in the form of the 37 percent aqueous solution which is the form most readily available commercially. However, the formaldehyde can also be used in one of its polymerized forms, i.e. as paraformaldehyde or trioxymethylene, if desired. The temperature at which the reactants are brought together is not critical. For the sake of convenience the reactants are generally brought together at ambient temperatures (circa 20° to 25° C) but higher or lower temperatures, from about 55° C down to about 10° C can be employed if desired. The reaction is exothermic but can be readily controlled either by appropriately adjusting the rate of addition of reactant or by applying external cooling, if necessary. Although, as indicated previously, the reaction temperature in this stage of the reaction is not critical it is preferable that the temperature of the reaction mixture does not rise above about 55° C during this phase of the reaction.

The reaction taking place beween the aniline and formaldehyde in this phase of the reaction is rather complex but the simplest reaction occurring can be represented by the following equation:

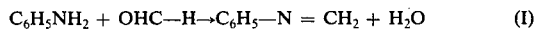

i.e. equimolar proportions of aniline and formaldehyde condense with the elimination of a molecule of water and the formation of the compound (I) which is variously known as "anhydroformaldehydeaniline" (see Cohn, supra) and as the anilinoacetal of formaldehyde.

As will be appreciated by one skilled in the art, the anilino acetal (I) can undergo further condensation. Illustratively the following reaction involving a second molecule of aniline can occur:

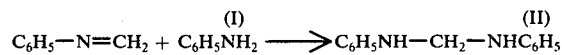

When the molar ratio of aniline to formaldehyde is at least 4:1, the latter compound (N,N'-diphenylmethylenediamine) is substantially the sole product present in this initial reaction. However, when lower proportions of aniline to formaldehyde are employed, the above material (II) may undergo reaction with a further molecule of aniline and of formaldehyde in accordance with the following equation:

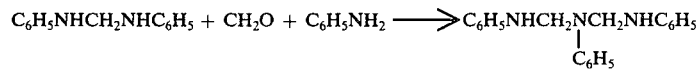

The product so obtained may undergo further similar condensation with formaldehyde and aniline to give more complex molecules. All of the reaction products so obtained including (II) can be described generically as anilinoacetals of formaldehydde or aminals for short, and will be so designated hereinafter.

Where an amount of aniline in excess of 2 moles, per mole of formaldehye, is employed in the process of the invention the reaction product obtained in the first step of said process is a mixture of (a) the above aminal (II) or a mixture of aminals and (b) excess aniline.

It has been found that the use of smaller proportions of aniline to formaldehyde than about 4 moles of aniline per mole of formaldehyde leads to the formation of significant amounts of undesirable by-products in the process of the invention. Chief of said by-products are the N-methyl substituted derivatives of the desired end products. Accordingly, when formation of such by-products is to be avoided, it is preferred to employ at least 4 moles of aniline per mole of formaldehyde. A most preferred ratio is one within the range of about 4 moles to about 6 moles of aniline per mole of formaldehyde.

While the lower limit of the molar proportion of aniline to formaldehyde employed in the first statge of the reaction is dictated by the desire to avoid the production of unrequired by-products, the upper limit is not critical and is dictated largely by economic considerations.

Generally speaking the proportion of aniline to formaldehyde employed in the first step of the process of the invention determines the proportion of di(aminophenyl)methane to higher polymethylene polyphenyl polyamines in the end-product. Thus, within limits, the higher the molar proportion of aniline to formaldehyde in the first step of the process of the invention the higher the proportion of di(aminophenyl)methane in the eventual reaction product. However, a proportion of about 10 moles of aniline to 1 mole of formaldehyde represents the practical upper limit of said proportions in the sense that it is not economical to employ higher proportions. Obviously, higher proportions can be employed without derogating from the overall results achieved in the process of the invention.

The reaction between the aniline and formaldehyde in the first step of the process of the invention occurs very rapidly even at ambient temperatures. The progress of the reaction can be followed by conventional analytical techniques, e.g. by following the disappearance of formaldehyde from the reaction mixture. When the reaction is observed to have proceeded to completion, the next stage of the process of the invention is initiated.

In the second stage of the process of the invention, the water of condensation eliminated in the first stage of the process is separated from the reaction mixture. Since the water separates as a distinct layer in the reaction mixture, the separation can be carried out simply by siphoning off or decanting the organic layer from the aqueous layer. However, in order to render the reaction mixture anhydrous the last traces of water have to be removed from the organic layer by distillation or like techniques. Accordingly, it is generally most convenient to carry out the separation of the organic and aqueous layers by simple distillation, long tube evaporation, and the like methods, under reduced pressure.

Advantageously, the mixture of animals, when freed from water as described above, contains not more than about 3.0% by weight of water and, preferably, contains not more than about 0.15% by weight of water.

In the next step of the process of the invention the anhydrous (i.e. having a water content below the limit set forth above) mixture of aminals is subjected to a three stage heating process, all the stages of which are carried out in the presence of a solid catalyst. The latter can be a diatomaceous earth, a zeolite or a clay. The diatomaceous earths are a well-known class of siliceous materials derived from diatoms and are inclusive of kieselguhr, tripolite, diatomite, infusorial earth and the like.

The clays employed in the process of the invention can be any of the clays conventionally employed in the catalytic art. Such clays include the naturally occurring and synthetic alumina silicates and are a well-recognized class of materials. Illustrative of such clays are: attapulgus clay, kaolins and montmorillonitic clays including fuller's earth, bentonite, montmorillonite and the like.

A wide variety of such clays is available commercially. For example, kaolin clays in various particle sizes are available from the J-M. Huber Corporation, Huber, Ga., and from Air Products and Chemicals, Inc. Bentonite clays in a variety of grades are available from the Georgia Kaolin Company, or under the trade name Filtrol from the Filtrol Corporation, Los Angeles, Calif. Montmorillonite clays mined in South Central Texas are available under the trade name Impact from The Milwhite Company, Houston, Tex.

The clays can generally be used in the state in which they are available commercially without any further treatment. However, it is generally found desirable to subject the clays to a drying process prior to use. Such drying can be accomplished by heating the clay, advantageously under nitrogen or under reduced pressure, to a temperature within the range of about 100° C to 500° C to remove some, or the bulk, of the occluded water in the clay.

A particularly preferred clay for use in the process of the invention is attapulgus clay.

The natural and synthetic zeolites, employed as catalysts in the process of the invention, are also a well-recognized class of materials. The synthetic zeolites are described, for example, in R. W. Grimshaw, The Chemistry and Physics of Clays, Fourth Edition Revised, 1971, pp. 168–9, Ernest Benn, Limited, London, and in D. W. Breck, Zeolite Molecular Sieves, John Wiley and Sons, N.Y. The zeolites are hydrated alumino-silicates having a relatively open crystal lattice which can be readily synthesized and which can be subjected to cation exchange to produce forms having different cations. Any of these known zeolites, in any of the different cation states, can be employed in the process of the invention. The naturally occurring zeolites are sodium and calcium aluminosilicates such as anocite, chabazite, heulandite, notrolite, stilbite, faujasite, and thomsonite; see, for example, Encyclopedia of Chemical Technology, Vol. 12, p. 295, 1954, Interscience Publishers Inc., New York, N.Y. A particularly useful group of zeolites for use in the present invention is the group of synthetic X and Y zeolites.

Advantageously the diatomaceous earth, clays or zeolites used in the process of the invention are employed in powder form. By this is meant that the average particle size of the solid catalyst is advantageously below about 20 microns (or above 65 mesh). A number of the solid catalysts of the invention are available in the form of pellets of various sizes, as extrudates, and as irregular granules, and such forms are particularly useful for continuous flow reactions which will be described hereinafter.

The amount of solid catalyst employed in the process of the invention is advantageously within the range of about 1 to about 50 percent by weight based on the mixture of aminals to be treated. Preferably, the amount of calcined acid clay or zeolite employed in the process of the invention is within the range of about 5 to about 10 percent by weight based on aminals.

In carrying out the three stage heating step of the process of the invention, the anhydrous mixture of aminals and the solid catalyst are brought together in any appropriate fashion. For example, the two components are mixed in any order and subjected to stirring in a batch type vessel. Alternatively, as will be discussed in more detail hereafter, the solid catalyst is suspended in a column and the aminal is allowed to percolate through the column of catalyst at any desired rate.

In the first of the three heating stages, the anhydrous mixture of aminals is maintained in contact with the catalyst, advantageously with vigorous agitation if the reaction is carried out on a batch basis, and the temperature of the reaction mixture is maintained within fairly close limits of the order of about 20° C to 55° C. These conditions are maintained until approximately 90% ± 10% by weight of the mixture of aminals has been converted to the corresponding benzylamines. This reaction is represented in the case of the simplest aminal, namely, N,N'-diphenylmethylenediamine (II), by the following reaction scheme:

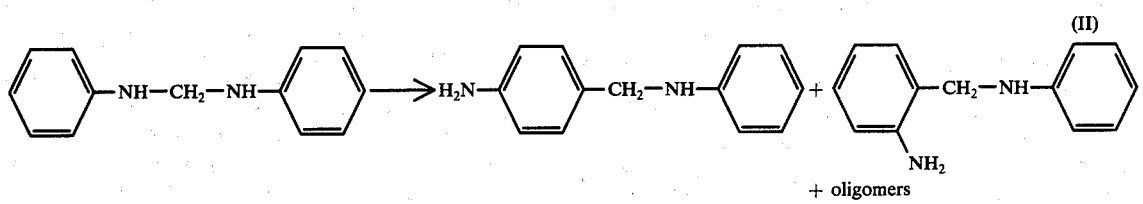

+ oligomers

As shown by the above scheme, the aminal (II) rearranges to form two isomeric N-(aminobenzyl)anilines and their oligomers. The more complex aminals rearrange in similar fashion to form correspondingly more complex benzylamines.

The progress of the conversion of the mixture of aminals to benzylamines can be followed readily by subjecting aliquots of the reaction mixture to conventional analytical procedures such as infrared spectroscopy, gas liquid phase chromatography, high pressure liquid chromatography, nuclear magnetic resonance spectroscopy, and the like. When the conversion of the mixture of aminals to benzylamines is observed to be about 90 ± 10 percent complete, the reaction mixture is then subjected to the second of the three stages of heat treatment. The elapsed time for conversion of the mixture of aminals to benzylzmines is generally of the order of about 20 minutes to about 300 minutes depending upon the actual reaction temperature (within the above stated range) and the proportions of reactants.

In the second stage of the heat treatment the mixture of benzylamines, residual aminals and solid catalyst is raised to a temperature of the range of about 55° to 65° C and is maintained thereat until the conversion of benzylamines to the desired di(aminophenyl)methanes is between 75 to 90 percent complete, i.e. the proportion of di(aminophenyl)methane and higher oligomers in the reaction mixture represents 75 to 90 percent by weight. The progress of the reaction can be followed by subjecting aliquots of the reaction mixture to routine analytical techniques such as those set forth above. The elapsed time for the conversion of the benzylamines to di(aminophenyl)methanes to reach the above stage is generally of the order of about 30 minutes to about 300 minutes depending, as before, upon the actual reaction temperature and the proportion of reactants in the mixture.

In the final stage of the heat treatment, the temperature of the reaction mixture is raised to, and maintained, within the range of about 80° to 100° C until the formation of di(aminophenyl)methane and higher oligomers is substantially complete. Again, the progress of the reaction is followed by subjecting aliquots of the reaction mixture to routine analytical procedures such as those set forth above. The elapsed time required for completion of this stage of the reaction to be completed is generally of the order of about 15 minutes to about 60 minutes depending upon the exact reaction temperature and proportion of reactants employed.

The reaction product so obtained is found to contain about 90 to 95 percent by weight of the diamine, i.e. di(aminophenyl)methane, the remainder of the mixture being higher oligomers the principal component of which is the triamine. Further, it is found that the high yield of the diamine is achieved without sacrificing the relatively high content (of the order of 85% by weight) of highly desirable 4,4'-isomer in the diamine. This is in marked contrast to previous processes employing heterogeneous catalysis of the aniline-formaldehyde reaction wherein not nly is the proportion of diamine obtained in the reaction mixture relatively low, but the proportion of the 4,4'-isomer in said diamine is also relatively low, often of the order of 60 percent or less. It is believed that this result, obtained in employing the prior art heterogeneous catalysis, is caused by carrying out the reaction of the formaldehyde and aniline in the presence of water and at temperatures in excess of about 100° C.

The mixture of diamines and higher oligomers obtained in accordance with the process of the invention can be treated in a variety of ways depending upon the ultimate use to which the various products are to be applied. For example, the mixture of polyamines is separated from the solid catalyst by filtration, centrifugation and like procedures and is then subjected to procedures such as fractional distillation under reduced pressure, fractional crystallization, and the like to separate the diamine content from the higher oligomers. The isolated diamine can be further purified, if desired, using fractional crystallization or like techniques to obtain a product which is substantially pure 4,4'-isomer. The isolated diamine, after purification if desired, can then be used as such, for example, as a curative for epoxy resins or as an intermediate in the formation, by catalytic hydrogenation, of di(aminocyclohexyl)methane, which latter is useful as intermediate, using methods well-known in the art, in the formation of polyamides, polyimides and copolymers thereof. The isolated diamine can also be phosgenated to form the corresponding diisocyanate which finds wide application in the preparation of polyurethane and like polymers.

The oligomeric polyamines which remain after separation of the diamine in the above manner contain mainly triamine which can be readily separated therefrom in pure state by fractional distillation. The triamine so isolated or the oligomeric polyamine mixture as whole, is useful as a curative for epoxy resins and as an intermediate in the production (by phosgenation) of the corresponding polymethylene polyphenyl polyisocyanates. The latter are widely known and used in the preparation of rigid polyurethane and polyisocyanurate foams and as adhesives and the like.

Alternatively, the mixture of diamine and oligomeric polyamines obtained in the process of the invention can be subjected, after stripping out any excess aniline but without separation of the individual components, to phosgenation to produce the corresponding mixture of methylenebis(phenyl isocyanates) and oligomeric polymethylene polyphenyl polyisocyanates. The mixture of isocyanates can be employed as such in the preparation of polyurethanes, polyisocyanurates and the like cellular and non-cellular polymers. On the other hand the mixture of isocyanates can be separated by fractional distillation into methylenebis(phenyl isocyanate) and a residue of the oligomeric polymethylene polyphenyl polyisocyanates. Illustrative of the procedures which can be employed for this separation are the continuous processes described in U.S. Pat. Nos. 3,471,543 and 3,892,634. The methylenebis(phenyl isocyanate) so obtained can be purified by fractional distillation to obtain substantially pure 4,4'-isomer. Because of the relatively high content of 4,4'-isomer present in the polyamines (and hence in the polyisocyanates) produced in accordance with the invention, the fractionation to give 4,4'-isomer is relatively easy. In contrast the products produced by previous methods of heterogeneous catalysis give too low a 4,4'-isomer content to enable fractionation to be carried out commercially.

In addition to separation of the diisocyanate in purified form using the above tecniques, the pure triisocyanate fraction can also be separated since this constitutes the bulk of the material other than diisocyanate in the product. The separation of triisocyanate in this manner from prior polymethylene polyphenyl polyisocyanates has not been practical because of the much lower proportion of triisocyanate to oligomers in the prior products. The ability to obtain pure triisocyanate, which has wide spread use in the preparation of adhesives and like non-cellular polyurethanes and polyisocyanurates, from the polyisocyanate mixture represents yet another advantage flowing from the process of the invention.

While the above description of the process of the invention has been given largely in terms of a batch type procedure, it will be obvious to one skilled in the art that the process can be carried out readily on a continuous basis. For example, the initial stage of mixing of formaldehyde and aniline is carried out in a continuous tubular reactor, the aminals so obtained are separated from water on a continuous basis, and the anhydrous animals are passed through a bed or column of the solid catalyst. The latter is maintained, for example, in a series of three zones maintained at temperatures corresponding to those desired in the final three stage heating stage. The rate of flow of reactants through the zones is adjusted so that the residence time of the reaction mixture in contact with the catalyst at any given temperature meets the requirements of the three stage heating process described hereinbefore. Other alternative ways of carrying out the process of the invention will be obvious to one skilled in the art.

The catalyst is found to maintain its activity over prolonged periods whether used in a continuous or batch type procedure. When the activity of the catalyst begins to deteriorate, it can be readily restored by heating at a temperature in the range of 100° C to 500° C for short periods of the order of 1 to 4 hours.

The process of the invention is possessed of a number of advantages. As previously noted, the process is free of the corrosion problems commonly associated with those prior art processes which employ mineral acid as catalyst and is accordingly very attractive to use on a commercial basis. More particularly the process gives rise to a product in which the diamine content is in excess of 90 percent by weight, a level which has not been attained heretofore by any commercially feasible process. Further, this high level of diamine in the product has been achieved without sacrifice of a significantly high content of 4,4'-isomer in the diamine. The results reported previously from the use of heterogeneous catalysts of the aniline-formaldehyde reaction have clearly indicated that the diamine to be obtained by the process would have a much lower level of 4,4'-isomer content and, hence, a much higher level of 2,4'-isomer content, than is found to be present in the product of the process of the present invention. The advantages flowing from this result have been discussed above.

A further highly useful result observed in regard to the process of the invention is that, not only is the proportion of higher oligomers in the reaction product remarkably lower than achieved hitherto, but the major portion of the oligomer fraction (i.e. at least 90 percent by weight) is found to be triamines, with only very minor amounts of higher oligomers.

This finding is particularly valuable since, in addition to the advantages discussed above of being able to isolate pure triamine and triisocyanate, it has a highly beneficial effect on the properties of the corresponding mixture of polymethylene polyphenyl polyisocyanates which is obtained by phosgenation of the mixture of polyamines obtained in accordance ith the process of the invention. Thus, the polyisocyanates have a lower isocyanate equivalent weight (more isocyanate per unit weight) than do corresponding products hitherto available in the art. The polyisocyanates also possess markedly lower viscosity than corresponding products hitherto known in the art which finding facilitates handling of the material and blending with other components of polymer forming mixtures. Equally importantly the polyisocyanates prepared as described above are significantly lighter in color and, more particularly, when used in the preparation of rigid polyurethane and like foams, give rise to products which are substantially white in color as opposed to the darkish brown foams hitherto derived from polyisocyanates of this type.

The following examples describe the manner and process of making and using the invention and set forth the best mode contemplated by the inventors of carrying out the invention but are not to be construed as limiting.

EXAMPLE 1 a. To a batch of 1679 g. (18 moles) of redistilled aniline, maintained in a glass flask cooled in an ice-bath, was added dropwise, with stirring, a total of 145.70 g. (1.8 moles) of 37% w/w aqueous formaldehyde solution over a period of 2 hr. The maximum temperature observed in the reaction mixture during the addition was 20° C. After the addition was complete, the reaction mixture was stirred for a further 3 hours at circa 25° C. The milky product so obtained was transferred to a separating funnel and allowed to stand overnight at circa 25° C. The organic phase was then separated and subjected to final drying by vacuum stripping at 50° C on a Rotafilm evaporator for 3 hours. The water content of the mixture of aminals so obtained was found by vapor phase chromatography to be 0.12 percent by weight.

b. A portion (71.04 g.) of the anhydrous aminal mixture prepared as described above was charged to a closed loop system comprising a vertical stainless steel column (27 × ½ inch o.d.) was packed with 33.36 g. of attapulgus clay (Pharmasorb activated attapulgite; pharmaceutical grade; Engelhard; which had previously been pelletized with 8% by weight of bleacheed wood binder, calcined at 500° C for 3 hours, ground in a mill and sieved to 30/60 mesh) and wrapped with a heating coil. Tubing (silicone and glass) was provided to conduct liquid flowing from the top of the column back to the base of the column via a pump. Stopcocks were provided in the tubing to serve as entry ports and exit ports. The aminal mixture was pumped to te base of the column and back to the pump at a flow rate of 2.0 cc/minute. The initial temperature in the column was 26° C and this was raised to 38° C during 16 minutes. The temperature in the column was thereafter maintained at 37° C to 40° C and samples of the circulating reaction mixture were withdrawn at approximately 10 minute intervals and subjected to analysis by nuclear magnetic resonance spectroscopy. It was found that a sample, taken 1 hour and 27 minutes after the column temperature initially reached 38° C, showed the presence of 100% benzylamines, there being no animals remaining or di(aminodiphenyl)methanes formed. The temperature of the column and contents was then raised to 60° C over a period of 5 minutes and was maintained thereat while samples of fluid reaction mixture were removed at approximately 10 minute intervals and subjected to analysis by nuclear magnetic resonance spectroscopy. A sample taken 3 hr. and 45 minutes after the temperature was first raised to 60° C showed that 77.7 percent by weight of the initial benzylamines had been converted to di(aminophenyl)methanes. Thereupon the temperature of the column and contents was raised over a period of 5 minutes to 96° C and was maintained at 96°-100° C for 35 minutes at the end of which time a sample indicated that formation of di(aminophenyl)methanes and oligomeric polyamines was substantially complete.

The resulting product was drained from the column and the column was washed with two portions, each of 40 cc., of methylene chloride. The methylene chloride was removed by distillation and the residue was combined with the material drained from the column; total weight = 51.87 g. indicating that a portion of reaction product remained absorbed in the column. The product so obtained was a mixture of aniline, di(aminophenyl)methane and higher oligomers of methylene polyphenyl polyamines. Gel permeation chromatography showed a proportion of 93.2 percent by weight of di(aminophenyl)methane to only 6.8 percent of higher oligomers. Of the latter oligomers, 90 percent by weight were triamines. The proportion of 4,4'-isomer in the diamine was 84.3% by weight, the proportion of 2,4'-isomer 14.4% and the proportion of 2,2'-isomer 1.3%, as measured by gas-liquid phase chromatography (glpc).

EXAMPLE 2

The procedure described in Example 1 was repeated but replacing the attapulgus clay employed in the stainless steel column by 34.3 g of diatomaceous earth (Floor-dry: Solamon Bros.; pulverized in a mill and sieved to 30/60 mesh).

A total of 69.90 g. of the anhydrous aminal mixture [prepared as described in Example 1, part (a)] was fed to the column and the temperature of the column was maintained at 38° ± 1° C with frequent sampling as described in Example 1 until conversion of aminals to benzylamines was observed to be 100% complete (by nuclear magnetic resonance spectroscopic analysis of the samples) at 1 hour and 52 minutes. Thereupon the temperature of the column and contents was raised to 64° – 65° C over a period of 3 minutes and was maintained thereat until, after 3 hours, the conversion of benzylamines to di(aminophenyl)methane was observed to be 79.7% complete. Finally, a this stage, the temperature of the column and contents was raised to 98.5° C to 100° C and maintained thereat for 30 minutes at the end of which time the nmr analysis of a sample showed 100% conversion to di(aminophenyl)methane and oligomers. The reaction product was removed from the column and the column washed with two portions of 40 cc. of chloroform. The chloroform washings were evaporated to dryness and the residue combined with the bulk of the product drained from the column. There was thus obtained 48.27 g. (some product still remained absorbed on the clay) of a mixture of aniline, di(aminophenyl)methane and hgher oligomeric methylene polyphenyl polyamines. Gel permeation chromatography showed that 94.3 percent by weight of the polyamines was di(aminophenyl)methane and 5.7 percent by weight was higher oligomers. Of the latter, 90 percent by weight were triamines. The proportion of 4,4'-isomer in the diamine was 85.2 percent by weight, the proportion of 2,4'-isomer was 13.6 percent by weight and the proportion of 2,2'-isomer was 1.2 percent by weight, as measured by glpc.

EXAMPLE 3

The procedure described in Example 1 was repeated but replacing the attapulgus clay there used in the stainless steel column by the same weight of an attapulgus clay (A RVM; Engelhard) previously dried at 150° C for 5 hr. under vacuum and sieved to 16/30 mesh.

A total of 66.68 g. of the anhydrous aminal mixture [prepared as described in Example 1, part (a)] was fed to the column and the temperature of the column was raised to 35° – 38° C and maintained thereat until nmr analysis of a sample indicated 100% conversion to benzylamines. The latter point was reached after 1 hr. and 15 minutes at the above temperatures. Thereupon the temperature of the column and contents was raised to 55° ± 1° C and maintained thereat until nmr analysis of a sample indicated 75 percent conversion to di(aminophenyl)methane and oligomers. This point was reached 2 hours and 38 minutes after the above temperature was attained. Finally, the temperature of the column and contents was raised to 90° C and maintained thereat for 22 minutes at the end of which time the nmr analysis of a sample indicated complete conversion to di(aminophenyl)methane and oligomers. The bulk (49.7 g.) of the product was isolated from the column as described in Example 1 as mixture of aniline, di(aminophenyl)methane and oligomeric methylene polyphenyl polyamines. Gel permeation chromatography showed that 94 percent by weight of the polyamines was di(aminophenyl)methane and 6 percent by weight was higher oligomers. Of the latter, 90 percent by weight was triamines. The proportion of 4,4'-isomer in the diamine was 83.1 percent by weight, the proportion of 2,4'-isomer was 15.2 percent by weight and the proportion of 2,2'-isomer was 1.7 percent by weight, as measured by glpc.

For purposes of comparison, the above experiment was repeated using the same reactants but omitting the first two temperatures stages and heating the column and contents directly to 90° C for a total of 25 minutes. The product obtained still contained 93.4 percent by weight of the polyamines in the form of di(aminophenyl)methane but the proportion of 4,4'-isomer in the diamine was substantially reduced to 75.2% by weight and the proportion of 2,4'-isomer was increased to 22.0% by weight, as measured by glpc.

In a second comparison experiment the process of the above Example 3 was repeated except that only two reaction temperature stages were employed in place of the three employed in Example 3. In the first stage the temperature of the column and contents was maintained at 38° C for 45 minutes at the end of which time the conversion of aminals to benzylamines was found to be substantially complete. The temperature of the column and contents was then raised to 80° C and maintained thereat for 30 minutes at the end of which time the conversion to di(aminophenyl)methane was found to be substantially complete. The product obtained still contained 94 percent by weight of the polyamines in the form of di(aminophenyl)methane but the proportion of 4,4'-isomer in the diamine was substantially reduced (78 percent by weight) and the proportion of 2,4'-isomer correspondingly increased (20.2 percent by weight), as measured by glpc.

EXAMPLE 4

This example follows very closely the conditions shown in Example 3 but employs different temperature levels in the second and third heating stages.

The procedure described in Example 1 part (b) was repeated by replacing the attapulgus clay there used in the stainless steel column by 33.85 g. of an attapulgus clay (A RVM; Engelhard) previously calcined for 3 hr. at 500° C.

A total of 66.49 g. of the anhydrous aminal mixture [prepared as described in Example 1, parts (a)] was fed to the column and the temperature of the column and contents was raised to 35° – 38° C and maintained thereat for 1 hr. at which time the nmr analysis of a sample indicated that conversion of aminal to benzylamines was substantially complete. The temperature of the column and contents was thereupon raised to 60° C and maintained thereat for 2 hr. and 17 minutes at which time the nmr analysis of a sample indicated that conversion of benzylamines to di(aminophenyl)methanes was 88 percent complete. Thereupon the temperature of the column and contents was raised to 100° C and maintained thereat for 15 minutes at the end of which time the conversion to di(aminophenyl)methanes was substantially complete as shown by the nmr analysis of a sample. The bulk of the product was isolated from the column by the procedure described in Example 1. Gel permeation chromatography of the product showed that 92.6 percent by weight of the polyamines in the product were di(aminophenyl)methanes and 7.4 percent by weight were oligomeric polyamines. Of the latter, 90 percent by weight were triamines. The proportion of the 4,4'-isomer in the diamines was 85 percent by weight, the proportion of 2,4'-isomer was 14 percent by weight and the proportion of 2,2'-isomer was 1 percent by weight, as measured by glpc.

EXAMPLE 5 a. Using the procedure described in Example 1 part (a), a mixture of aminals was obtained by reaction of 312.9 g. (3.36 moles) of redistilled aniline and 45.53 g. (0.56 moles) of 37% w/w aqueous formaldehyde solution. After separation of the aqueous phase as described in Example 1, part (a), but without drying, the mixture of aminals was found by glpc to contain 2.7% by weight of water. A portion of this "wet" aminal mixture was retained and treated as described in (c) below and the bulk of the aminal mixture was subjected to stripping using a Rotafilm evaporator under vacuum for 2 hr. at 45° C. After this treatment, the water content of the aminal mixture was found by glpc to be 0.13% by weight.

b. A portion (69.35 g.) of the above vacuum-dried aminal mixture was then subjected to the three stage heating process described in Example 1, part (b). The stainless steel column was packed with attapulgus clay (A RVM; Engelhard) previously calcined at 500° C for 3 hr., but otherwise the apparatus and procedure were the same as that described in Example 1, part (b). The initial stage was carried out with the temperature of the column and contents at 38° ± 1.5° C and, after 80 minutes at this temperature, it was found by nmr analysis of a sample that conversion of aminals to benzylamines was substantially complete. The temperature of the column and contents was then raised to 60° ± 1.0° C and maintained thereat for 2 hr. and 43 minutes at the end of which time the conversion of benzylamines to di(aminophenyl)methane and oligomers was 89% complete. The temperature of the column and contents was thereupon raised to 100° C and maintained thereat for 15 minutes at the end of which time the conversion of benzylamines to di(aminophenyl)methane and oligomers was found by nmr analysis to be 100% complete.

The bulk of the product (56.84 g.) was isolated from the column using the procedure described in Example 1, part (b). There was thus obtained a mixture of aniline, di(aminophenyl)methane and oligomeric methylene polyphenyl polyamines. Gel permeation chromatography of the product showed that 90.7 percent by weight of the polyamines in the product were di(aminophenyl)methanes and 9.1 percent by weight were oligomeric polyamines. Of the latter, 90 percent by weight were triamines. The proportion of the 4,4'-isomer in the diamines was 82.7 percent, the proportion of the 2,4'-isomer was 16.0 percent and the proportion of 2,2'-isomer was 1.3 percent, by glpc.

c. In order to show the effect of water on the process of the invention, the procedure set forth in part (b) above was repeated using the "wet" mixture of aminals obtained as described in part (a), i.e. the aminal mixture containing 2.7 percent by weight of water. A total of 67.39 g. of this "wet" aminal mixture was subjected to three stage heat treatment using an identical clay column and a procedure identical to that described in part (b) above. The first stage heating was carried out at 38° ± 1° C and required 2 hr. and 30 minutes [as opposed to 80 minutes in the process of part (b)] to effect 96 percent conversion of aminals to benzylamines. Since the nmr analysis of the sample taken at this stage already showed the formation of a trace of di(aminophenyl)methane the temperature of the column and contents was raised to the second level, namely 69° ± 1° C, and maintained thereat for 60 minutes at the end of which time the conversion of benzylamines to di(aminophenyl)methanes and oligomers was found to be 89 percent complete. Thereupon, the temperature of the column and contents was raised to 100° – 101° C and maintained thereat for 30 minutes until nmr analysis of a sammple showed conversion to di(aminophenyl)methane and oligomers to be complete. The bulk of the product (54.05 g.) was recovered from the column using the procedure described in Example 1, part (b) to obtain a mixture of aniline, di(aminophenyl)methane and oligomeric methylene polyphenyl polyamines. Gel permeation chromatography analysis of the product showed that 90.1 percent by weight of the polyamines in the product were di(aminophenyl)methanes and 9.9 percent by weight were oligomeric polyamines. The proportion of the 4,4'-isomer in the diamines was 77.0 percent by weight, the proportion of the 2,4'-isomer was 21.3 percent by weight and the proportion of the 2,2'-isomer was 1.7 percent by weight, as measured by glpc.

EXAMPLE 6

This example illustrates the phosgenation of methylene polyphenyl polyamines, made in accordance with the process of the invention, to obtain the corresponding polyisocyanates.

The amine mixture employed as starting material was obtained by blending i. 54.23 g. of the amine mixture obtained as described in Example 5, part (b) with
ii. 45.46 g. of an amine mixture obtained in a duplicate of the run described in Example 5, part (c) with the exception that the temperature in the first stage was 45° C, maintained for 70 minutes, and the temperature in the second stage was 60° to 65° C, maintained for 280 minutes. This amine mixture was found by gel permeation chromatography to contain 90.4 percent by weight of diamine and 9.6 percent by weight of oligomeric polyamines.

The blend of the two amine mixtures was subjected to steam distillation to remove excess aniline and the residue was extracted with 3 portions, each of 100 ml., of chloroform. The combined chloroform extracts were dried over anhydrous sodium sulfate and then evaporated to dryness. The residual amine mixture (35.36 g.) was found by gel permeation chromatography to contain 90.0 percent by weight of diamine and 10.0 percent by weight of oligomeric polyamines. The diamine was found, by vapor phase chromatography, to contain 82.0 percent by weight of 4,4'-isomer, 16.6 percent by weight of 2,4'-isomer and 1.3 percent by weight of 2,2'-isomer.

The phosgenation procedure was as follows:

A total of 250.5 g. of gaseous phosgene was passed into 200 cc. of anhydrous toluene, maintained at 2° to 5° C, over a period of 90 minutes. To the phosgene solution so obtained was added, with stirring, a solution of 25 g. of the above amine mixture in 100 cc. of anhydrous toluene. The mixture was maintained at −5° C during the addition which required approximately 30 minutes. The resulting slurry was stirred for a further 0.5 hr. while being cooled in an ice bath. At the end of this time the ice bath was removed and stirring was continued while the reaction mixture reached room temperature (circa 20° C). The temperature of the reaction mixture was then gradually raised to 55° to 60° C whereupon vigorous decomposition ensued. The temperature of the reaction mixture was slowly raised to 90° C and a slow stream of phosgene was introduced into the mixture and was continued while the temperature reached reflux and was held thereat for approximately 3 hr. At the end of this period the reaction mixture was purged with nitrogen for 1.5 hr. and then subjected to distillation under reduced pressure to remove solvent. When the volume of the reaction mixture had been reduced by about 25 percent, the distillation was interrupted while the solution was filtered to remove a small amount of insoluble material. The filtrate was then distilled under reduced pressure to remove the excess solvent, the final flask temperature being 125° C at 0.025 mm., which condtions were maintained for 1 hr. There was thus obtained 28.2 g. of a mixture of methylenebis(phenyl isocyanate) and oligomeric isocyanates having a viscosity of 25 cts. at 25° C and an isocyanate equivalent of 131. The proportion of diisocyanate present in the mixture was found by gel permeation chromatography to be 76.7 percent by weight and the proportion of oligomeric polyisocyanates was 23.3 percent by weight. The diisocyanate was found by gas liquid phase chromatography to contain 81.0 percent by weight of 4,4'-isomer, 17.3 percent by weight of 2,4'-isomer and 1.7 percent by weight of 2,2'-isomer.

We claim:

1. A process for the preparation of a mixture of di(aminophenyl)methane and oligomeric polymethylene polyphenyl polyamines wherein the diamine content is of the order of 90 percent by weight and wherein the p,p'-isomer content of said diamine is of the order of 85 percent by weight which process comprises the steps of
   a. reacting aniline and formaldehyde in a proportion within the range of 2 moles to 10 moles of aniline per mole of formaldehyde at a temperature of 10° C to 55° C and in the absence of acid catalyst to form a mixture of aminals;
   b. separating the water from said aminals;
   c. contacting said aminals, free from water, with a solid catalyst selected from the class consisting of diatomaceous earth, clay, and zeolite at a temperature of 20° C to 55° C until the reaction mixture contains from about 80% to 100% by weight of the corresponding benzylamines;
   d. thereafter adjusting the temperature of the reaction mixture to about 55° C to 65° C until from about 75% to 90% by weight of said benzylamines have been converted to methylene polyphenyl polyamines; and
   e. thereupon finally raising the temperature of the reaction mixture to 80° C to 100° C until conversion to methylene polyphenyl polyamines is complete.

2. The process of claim 1 wherein the molar proportion of aniline to formaldehyde employed is within the range of about 4:1 to about 6:1.

3. The process of claim 1 wherein the removal of water from the mixture of aminals in step (b) is completed by distillation of said water from said mixture of aminals under reduced pressure at a temperature not exceeding 55° C until the water content of said aminal is not greater than 0.15% by weight.

4. The process of claim 1 wherein the catalyst is attapulgus clay.

5. The process of claim 1 wherein the catalyst is a zeolite.

6. The process of claim 1 wherein the catalyst is diatomaceous earth.

7. A process according to claim 1 wherein the solid catalyst has been subjected to drying by heating at a temperature in the range of 100° C to 500° C prior to use.

8. A process for the preparation of a mixture of di(aminophenyl)methane and oligomeric polymethylene polyphenyl polyamines wherein the diamine content is of the order of 90 percent by weight and wherein the p,p'-isomer content of said diamine is of the order of 85 percent by weight, which process comprises the steps of
   a. reacting aniline and formaldehyde in a proportion within the range of 4 moles to 6 moles of aniline per moel of formaldehyde at a temperature of 10° C to 55° C and in the absence of acid catalyst to form a mixture of aminals;
   b. separating the water from said aminals;
   c. contacting said aminals, free from water, with a diatomaceous earth catalyst at a temperature of 20° C to 55° C until the reaction mixture contains from about 80 to 100% by weight of the corresponding benzylamines;
   d. thereafter adjusting the temperature of the reaction mixture to 55° C to 65° C until from about 75% to 90% by weight of said benzylamines have been converted to methylene polyphenyl polyamines; and
   e. thereupon finally raising the temperature of the reaction mixture to 80° C to 100° C until conversion to methylene polyphenyl polyamines is complete.

9. A process according to claim 8 wherein the diatomaceous earth has been subjected to drying by heating at a temperature in the range of 100° C to 500° C prior to use.

10. A process according to claim 8 wherein the removal of water from the mixture of aminals in step (b) is completed by distillation of said water from said mixture of aminals under reduced pressure at a temperature not exceeding 55° C until the water content of said aminal is not greater than 0.15% by weight.

11. A process for the preparation of a mixture of di(aminophenyl)methane and oligomeric polymethylene polyphenyl polyamines wherein the diamine content is of the order of 90 percent by weight and wherein the p,p'-isomer content of said diamine is of the order of 85 percent by weight, which process comprises the steps of
   a. reacting aniline and formaldehyde in a proportion within the range of 4 moles to 6 moles of aniline per mole of formaldehyde at a temperature of 10° C to 55° C and in the absence of acid catalyst to form a mixture of aminals;
   b. separating the water from said aminals;
   c. contacting said aminals, free from water with an attapulgus clay catalyst at a temperature of 20° C to 55° C until the reaction mixture contains from about 80 to 100% by weight of the corresponding benzylamines;
   d. thereafter adjusting the temperature of the reaction mixture to 55° C to 65° C until from about 75% to 90% by weight of said benzylamines have been converted to methylene polyphenyl polyamines; and
   e. thereupon finally raising the temperature of the reaction mixture to 80° C to 100° C until conversion to methylene polyphenyl polyamines is complete.

12. A process according to claim 11 wherein the attapulgus clay has been subjected to drying by heating at a temperature in the range of 100° C to 500° C prior to use.

13. A process according to claim 11 wherein the removal of water from the mixture of aminals instep (b) is completed by distillation of said water from said mixture of aminals under reduced pressure at a temperature not exceeding 55° C until the water content of said aminal is not greater than 0.15% by weight.

* * * * *